United States Patent [19]

Darwent et al.

[11] Patent Number: 4,904,406
[45] Date of Patent: Feb. 27, 1990

[54] QUATERNARY AMMONIUM COMPOUNDS FOR USE IN BLEACHING SYSTEMS

[75] Inventors: James R. Darwent, West Kirby; Keith C. Francis, Oxton; John Oakes, Winsford; David W. Thornthwaite, Neston, all of Great Britain

[73] Assignee: Lever Brothers Company, New York, N.Y.

[21] Appl. No.: 313,112

[22] Filed: Feb. 21, 1989

[30] Foreign Application Priority Data

Mar. 1, 1988 [GB] United Kingdom ................. 8804816
Nov. 14, 1988 [GB] United Kingdom ................. 8826619

[51] Int. Cl.$^4$ ....................... C11D 3/395; D06L 3/02; C01B 15/00; C01B 15/055
[52] U.S. Cl. ...................................... 252/102; 252/99; 252/186.22; 252/186.23; 252/186.38; 252/186.39; 252/186.41; 252/186.42
[58] Field of Search ....................... 252/186.23, 186.21, 252/186.22, 186.38, 186.39, 186.41, 186.42, 102

[56] References Cited

U.S. PATENT DOCUMENTS

| | | | |
|---|---|---|---|
| 3,256,198 | 6/1966 | Matzner | 252/99 |
| 3,272,750 | 9/1966 | Chase | 252/99 |
| 4,397,757 | 8/1983 | Bright et al. | 252/186.41 |
| 4,412,934 | 11/1983 | Chung et al. | 252/186.38 |
| 4,486,327 | 12/1984 | Murphy et al. | 252/94 |
| 4,751,015 | 6/1988 | Humphreys et al. | 252/99 |
| 4,818,426 | 6/1988 | Humphreys et al. | 252/99 |

FOREIGN PATENT DOCUMENTS

| | | |
|---|---|---|
| 0098129 | 1/1984 | European Pat. Off. . |
| 0120591 | 10/1984 | European Pat. Off. . |
| 166571 | 1/1986 | European Pat. Off. . |
| 0170386 | 2/1986 | European Pat. Off. . |
| 0284292 | 9/1988 | European Pat. Off. . |
| 0303520 | 2/1989 | European Pat. Off. . |
| 0836988 | 6/1960 | United Kingdom . |
| 0907356 | 10/1962 | United Kingdom . |

Primary Examiner—Brooks H. Hunt
Assistant Examiner—Virginia B. Caress
Attorney, Agent, or Firm—Milton L. Honig

[57] ABSTRACT

A quaternary ammonium-substituted peroxycarboxylic acid bleach precursor, its quaternary ammonium peroxycarboxylic acid derivative, and bleaching-detergent compositions containing these materials are disclosed herein. The bleach precursor structurally comprises a quaternized ammonium group linked to a carboxyl moiety having a leaving group via an aromatic or heterocyclic bridging group which, upon perhydrolysis in the presence of hydrogen peroxide, generates a highly effective, quaternary ammonium-substituted aromatic or heterocyclic peroxycarboxylic acid bleach.

6 Claims, No Drawings

QUATERNARY AMMONIUM COMPOUNDS FOR USE IN BLEACHING SYSTEMS

FIELD OF THE INVENTION

This invention relates to new quaternary ammonium-substituted peroxycarboxylic acid precursors of use in bleaching systems. The bleach systems of the invention may be used in combination with a detergent active system.

PRIOR ART AND BACKGROUND TO THE INVENTION

It is well known that active oxygen-releasing peroxide compounds are effective bleaching agents. These compounds are frequently incorporated in detergent compositions for stain and soil removal. They have, however, an important limitation: the activity is extremely temperature-dependent. Thus, active oxygen-releasing bleaches are essentially only practical when the bleaching solution is heated above 60° C. At a bleach solution temperature of about 60° C., extremely high amounts of the active oxygen-releasing compounds must be added to achieve any bleaching effect. This is both economically and practically disadvantageous. As the bleach solution temperature is lowered below 60° C., peroxide compounds, e.g. sodium perborate, are rendered ineffective, regardless of the level of peroxide compound added to the system. The temperature dependency of peroxide compounds is significant because such bleach compounds are commonly used as a detergent adjuvant in textile wash processes that utilize an automatic household washing machine operating at wash water temperatures of 60° C. and therebelow. Such wash temperatures are utilized because of textile care and energy considerations. Consequently, a constant need has developed of substances which render peroxide compound bleaches more effective at bleach solution temperatures below 60° C. These substances are generally refered to in the art as bleach precursors, promoters or activators.

Normally, bleach precursors are used in conjunction with peroxide compounds, e.g. persalts, which are capable of releasing hydrogen peroxide in aqueous solution, perborate being the most widely used persalt.

Typically, the precursor is a reactive compound such as a carboxylic acid ester that in alkaline solution containing a source of hydrogen peroxide, e.g. a persalt, such as sodium perborate, will generate the corresponding peroxyacid. The reaction involves nucleophilic substitution onto the precursor by hydroperoxy anions (HOO⁻) and is facilitated by precursors having good leaving groups. Often the reaction is referred to as a perhydrolysis.

Examples of bleach precursors are carboxylic esters as disclosed in UK patent specification 836,988; EP-A-0098129 and EP-A-0120591; organic acyl amides as disclosed in UK patent specification 907,356; and organic carbonate esters as disclosed in U.S. Pat. Nos. 3,256,198 and 3,272,750. Quaternary ammonium peroxycarboxylic acid precursors are also known from UK patent specification 1,382,594. The compounds as described in this prior art reference are of the formula:

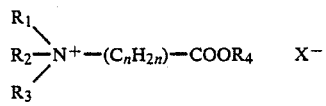

wherein
—$(C_nH_{2n})$— is an optionally branched chain having n equal to 3 or more, preferably 3 to 25;
$R_1$ is an optionally substituted alkyl radical containing from 1 to 20 carbon atoms, alkaryl, optionally substituted aryl or polyoxyalkylene radical;
$R_2$ and $R_3$ are each lower alkyl or hydroxylalkyl radical containing from 1 to 4 carbon atoms;
or two or more of $R_1$, $R_2$ and $R_3$ together with the N-atom form an optionally substituted, nitrogen-containing heterocyclic ring system;
$R_4$ is an optionally substituted phenyl group;
X is chlorine or bromine.

Typical quaternary ammonium compounds according to this reference are:
N-octyl, N,N-dimethyl N-10 carbophenoxydecyl ammonium chloride (ODC);
N-octyl, N,N-dimethyl N-10 carbophenoxydecyl ammonium bromide (ODB); and
N-10 carbophenoxydecyl pyridinium bromide (PDB) or chloride (PDC).

A drawback of these quaternary ammonium compounds of the art is that their effectiveness in wash/bleach solutions is rather inconsistent, which could be caused by the fact that the peroxycarboxylic acids derived therefrom are sensitive to temperature and formulation ingredients.

It is an object of the present invention to provide novel quaternary, ammonium-substituted peroxycarboxylic acid precursors, of which the peracids generated therefrom are more stable to temperature and towards composition ingredients present in the wash/bleach solution.

It is another object of the present invention to provide a detergent bleach composition with a precursor that permits highly effective bleaching over a wide temperature range, including that of under 40° C.

DESCRIPTION OF THE INVENTION

The novel quaternary ammonium-substituted peroxycarboxylic acid precursors of the invention have the formula:

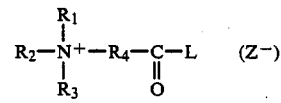

wherein
$R_1$, $R_2$ and $R_3$ are each a radical selected from the group consisting of optionally substituted alkyl, alkenyl, hydroxyalkyl and polyoxyalkylene containing from 1 to 18 carbon atoms;
or two of $R_1$, $R_2$ and $R_3$ together with $R_4$ and the N-atom form an optionally substituted, nitrogen-containing heterocyclic ring system;
or two or more of $R_1$, $R_2$ and $R_3$ together with the N-atom form an optionally substituted, nitrogen-containing heterocyclic ring system;

R₄ (if not formed into a nitrogen-containing heterocyclic ring system together with R₁ and/or R₂ and/or R₃) is a bridging group selected from

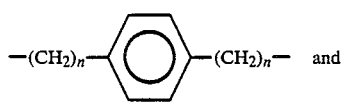

and

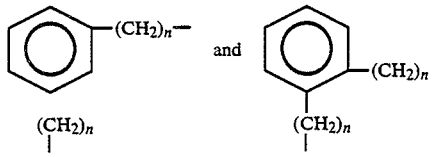

wherein
each n individually can be 0, 1 or 2;
L is a leaving group, the conjugate acid of which has a $pK_a$ in the range of from 4 to 13, preferably from about 8 to 10; and
$Z^-$ can be a chloride, bromide, hydroxide, nitrate, methosulphate, bisulphate, acetate, sulphate, citrate, borate or phosphate anion.

It should be appreciated that the presence of ($Z^-$) as counter ion is not essential and that compounds without this counter ion are also feasible and within the purview of the present invention.

Many and diverse leaving group structures have been described in the patent literature and may be useful for the purpose of this invention. For example, U.S. Pat. Nos. 4,412,934 and 4,486,327, EP-A-170,386 and EP-A-166,571 provide examples of desirable leaving groups.

Illustrative of leaving group structures L are those selected from the group consisting of:

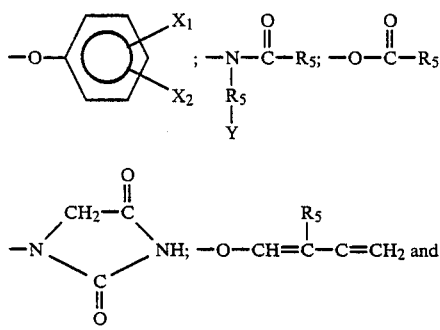

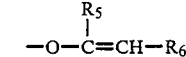

wherein
$X_1$ and $X_2$ are each individually H or a substituent selected from $-SO_3^-M^+$; $-COO^-M^+$; $-SO_4^-M^+$; $(-N^+R_1R_2R_3)Z^-$; $-NO_2$; and $C_1-C_8$ alkyl groups; $R_5$ is a $C_1-C_{12}$ alkyl group; $R_6$ is H or $R_5$ and Y is H or $-SO_3^-M^+$, $-COO^-M^+$, $-SO_4^-M^+$, $(N^+R_1R_2R_3)Z^-$ or $-NO_2$;
M is a hydrogen, alkali metal, ammonium, or alkyl or hydroxyalkyl-substituted ammonium cation, which may or may not be present.

Of these the most preferred leaving group is

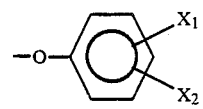

and hence the novel peroxycarboxylic acid precursors of the invention will preferably have the formula:

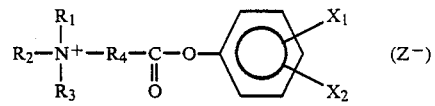

wherein $R_1$, $R_2$, $R_3$, $R_4$, $X_1$ and $X_2$ and Z are as defined hereinabove.

Preferred compounds are those wherein $R_1$, $R_2$ and $R_3$ are $C_1-C_4$ alkyl chains, preferably methyl, and wherein $X_1$ is hydrogen and $X_2$ is $-SO_3^-M^+$ or $-COO^-M^+$.

A quaternary ammonium peroxycarboxylic acid is also provided having the formula:

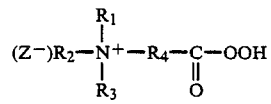

wherein $R_1$, $R_2$, $R_3$, $R_4$ and $Z^-$ are as defined above.

As such the following classes of compounds are representative of the precursors within the concept of the present invention:

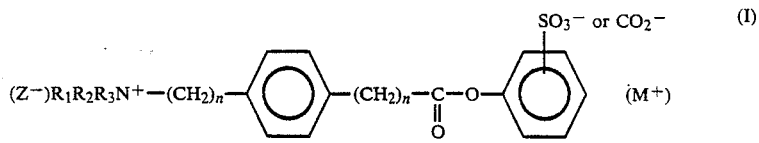

(I)

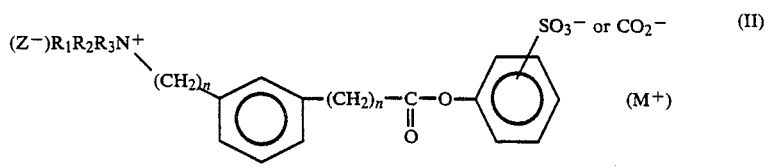

(II)

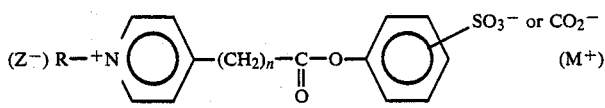
(III)

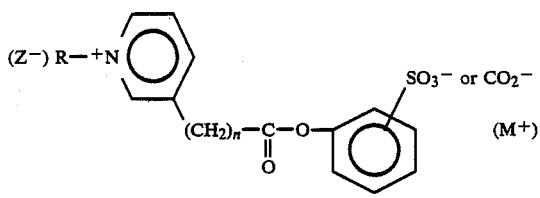
(IV)

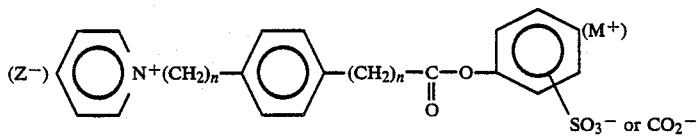

Preferred compounds are those of classes I, II and III and typical examples thereof are:

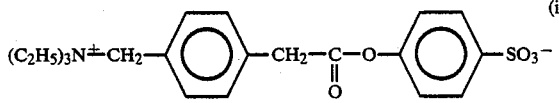 (i)

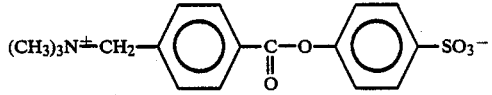 (ii)

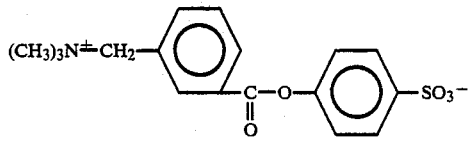 (iii)

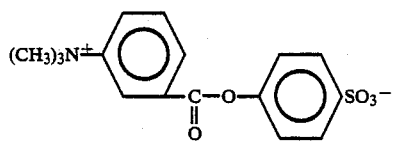 (iv)

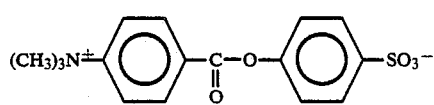 (v)

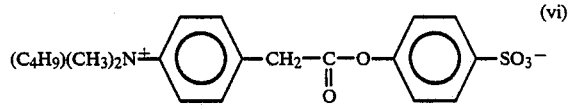 (vi)

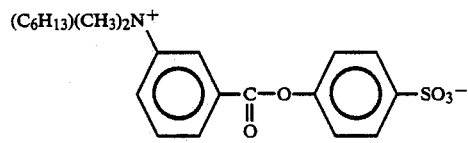 (vii)

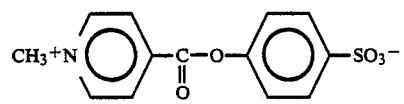 (viii)

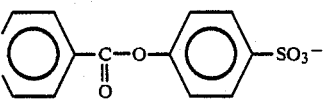 (ix)

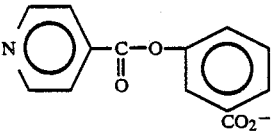 (x)

Especially preferred compounds are compounds (i), (ii), (iii) and (iv) because of their ease of potential scale-up production.

Quaternary ammonium peroxyacids generated from these novel precursors in combination with hydrogen peroxide or a persalt, show higher bleach efficacy upon fabrics than expected on the basis of their hydrophobic properties (log P), with bleaching rate constants that are many times higher than peracetic acid. Furthermore, the precursors of the invention generate peroxycarboxylic acids, e.g.

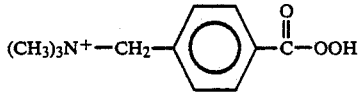

that are more stable to temperature and formulation ingredients (e.g. borates) than those generated from quaternary ammonium peroxycarboxylic acid precursors of the art.

The foregoing precursors may be incorporated in bleach compositions which require as an essential component a peroxide bleaching compound capable of yielding hydrogen peroxide in an aqueous solution.

In such compositions the molar ratio of hydrogen peroxide (or a peroxide compound generating the equivalent amount of hydrogen peroxide) can generally be varied within a range of from about 0.5:1 to about 25:1. In preferred embodiments of this aspect of the invention the molar ratio will range from 1:1 to about 15:1. Hydrogen peroxide sources are well known in the art. They include the alkali metal peroxides, organic peroxide bleaching compounds, such as urea peroxide, and inorganic persalt bleaching compounds, such as the alkali metal perborates, percarbonates, perphosphates and persulphates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous bleaching solutions. Rapid dissolution is believed to permit formation of higher levels of peroxycarboxylic acid which would enhance surface bleaching performance.

A detergent formulation containing a bleach system consisting of an active oxygen-releasing material and a novel compound of the invention will usually also contain surface-active materials, detergency builders and other known ingredients of such formulations.

In such formulations the peroxycarboxylic acid precursor of the invention may be present at a level ranging from about 0.1% to 20% by weight, preferably from 0.5% to 10% by weight, particularly from 1% to 7.5% by weight, together with a peroxide bleaching compound, e.g. sodium perborate mono- or tetrahydrate, the amount of which is usually within the range of from about 2% to 40% by weight, preferably from about 4% to 30% by weight, particularly from about 10% to 30% by weight.

The surface-active material may be naturally derived, such as soap, or a synthetic material selected from anionic, nonionic, amphoteric, zwitterionic, cationic actives and mixtures thereof. Many suitable actives are commercially available and are fully described in literature, for example in "Surface Active Agents and Detergents", Volumes I and II, by Schwartz, Perry and Berch. The total level of the surface-active material may range up to 50% by weight, preferably being from about 1% to 40% by weight of the composition, most preferably 4 to 25%.

Synthetic anionic surface-actives are usually water-soluble alkali metal salts of organic sulphates and sulphonates haing alkyl radicals containing from about 8 to about 22 carbon atoms, the term alkyl being used to include the alkyl portion of higher aryl radicals.

Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$)benzene sulphonates; sodium alkyl glyceryl ether sulphates, especially those esters of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxides per molecule; the condensation products of aliphatic ($C_8$–$C_{18}$) primary or secondary linear or branched alcohols with ethylene oxide, generally 6–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides. Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated in the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or, less desirably, potassium salts of saturated or unsaturated $C_{10}$–$C_{24}$ fatty acids or mixtures thereof. The amount of such soaps can be varied between about 0.5% and about 20% by weight, with lower amounts of about 0.5% to about 5% being generally sufficient for lather control. Amounts of soap between about 2% and about 20%, especially between about 5% and about 15%, are used to give a beneficial effect on detergency. This is particularly valuable in compositions used in hard water when the soap acts as a supplementary builder .

The detergent compositions of the invention will normally also contain a detergency builder. Builder materials may be selected from (1) calcium sequestrant materials, (2) precipitating materials, (3) calcium ion-exchange materials and (4) mixtures thereof.

Examples of calcium sequestrant builder materials include alkali metal polyphosphates, such as sodium tripolyphosphate; nitrilotriacetic acid and its water-soluble salts; the akali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate, sodium carbonate and long chain fatty acid soaps.

Examples of calcium ion-exchange builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethyl malonate, carboxymethyloxy succinate and the water-insoluble crystalline or amorphous aluminosilicate builder materials, or mixtures thereof.

These builder materials may be present at a level of, for example, from 5 to 80% by weight, preferably from 10 to 60% by weight.

Apart from the components already mentioned, the detergent compositins of the invention can contain any of the conventional additives in the amounts in which such materials are normally employed in fabric washing detergent compositions. Examples of these additives include lather boosters, such as alkanolamides, particularly the monoethanol amides derived from palmkernel fatty acids and coconut fatty acids, lather depressants, such as alkyl phosphates and silicones, anti-redeposition agents, such as sodium carboxymethyl cellulose and alkyl or substituted alkyl cellulose ethers, other stabilizers, such as ethylene diamine tetraacetic acid, fabric softening agents, inorganic salts, such as sodium sulphate, and, usually present in very small amounts, fluorescent agents, perfumes, enzymes, such as proteases, cellulases, lipases and amylases, germicides and colourants.

The bleach precursors and their peroxycarboxylic acid derivatives described herein are useful in a variety of cleaning products. These include laundry detergents, laundry bleaches, hard surface cleaners, toilet bowl cleaners, automatic dishwashing compositions and even denture cleaners. Precursors of the present invention can be introduced in a variety of product forms including powders, on sheets or other substrates, in pouches, in tablets or in non-aqueous liquids, such as liquid nonionic detergents.

Generally, the bleach precursors will advantageously be presented in the form of particulate bodies comprising said bleach precursor and a binder of agglomerating agent. Many and diverse methods of preparing such precursor particulates have been described in various patent literature documents, such as e.g. in Canadian Patent 1,102,966; GB Patent No. 1,561,333; U.S. Pat. No. 4,087,369; EP-A-0,240,057; EP-A-0,241,962; EP-A-0,101,634 and EP-A-0,062,523. Each of these methods may be selected and applied to the bleach precursor of the invention.

Particulates incorporating the precursors of the present invention are normally added to the spray-dried portion of the detergent composition with the other dry-mix ingredients, such as enzymes, inorganic peroxygen bleaches and suds depressants. It will be appreciated, however, that the detergent composition to which the precursor particulates are added may itself be made in a variety of ways, such as dry-mixing, agglomeration extrusion, flaking etc., such ways being well known to those skilled in the art and not forming part of the present invention.

The peroxyacid precursors of the present invention can also be incorporated in detergent additive products.

Such additive products are intended to supplement or boost the performance of conventional detergent compositions and may contain any of the components of such compositions, although they will not comprise all of the components present in a fully formulated detergent composition. Additive products in accordance with this aspect of the invention will normally be added to an aqueous liquor containing a source of (alkaline) hydrogen peroxide, although under certain circumstances a source of alkaline hydrogen peroxide may be included in the product.

Additive products in accordance with this aspect of the present invention may comprise the compound alone in combination with a carrier, such as a compatible particulate substrate, a flexible non-particulate substrate or a container. Examples of compatible particulate substrates include inert materials, such as clays and other aluminosilicates including zeolites, both natural and synthetic of origin. Other compatible particulate carrier materials include hydratable inorganic salts, such as phosphates, carbonates and sulphates.

Additive products enclosed in bags or containers may be of such type that the containers prevent egress of their contents when dry but are adapted to release their contents on immersion in an aqueous solution.

In a further specific embodiment, the quaternary ammonium-substituted peroxy carboxylic acid precursor compounds of the invention are particularly suitable for incorporation in so-called non-aqueous liquid laundry detergent compositions together with a peroxide bleaching compound, e.g. sodium perborate, to impart an effective cleaning and stain-removing capacity to the products on fabrics and textiles.

Non-aqueous liquid detergent compositions including paste-like and gelatinous detergent compositions in which the precursor compounds can be incorporated are known in the art and various formulations have been proposed, e.g. in U.S. Pat. Nos. 2,864,770; 2,940,938; 4,772,412; 3,368,977; GB-A-1,205,711; 1,270,040; 1,292,352; 1,370,377; 2,194,536; DE-A-2233771; and EP-B-0028849.

These are compositions which normally comprise a non-aqueous liquid medium with or without a solid phase dispersed therein. The non-aqueous liquid medium may be a liquid surfactant, preferably a liquid nonionic surfactant; a non-polar liquid medium, e.g. liquid paraffin; a polar solvent, e.g. polyols, such as glycerol, sorbitol, ethylene glycol, optionally combined with low-molecular monohydric alcohols, e.g. ethanol or isopropanol; or mixtures thereof.

The solid phase can be builders, alkalis, abrasives, polymers, clays, other solid ionic surfactants, bleaches, enzymes, fluorescent agents and other usual solid detergent ingredients.

The precursor compounds of the invention may be prepared and synthesized by way of the following chemical reaction schemes:

SCHEME 1

Synthesis of:

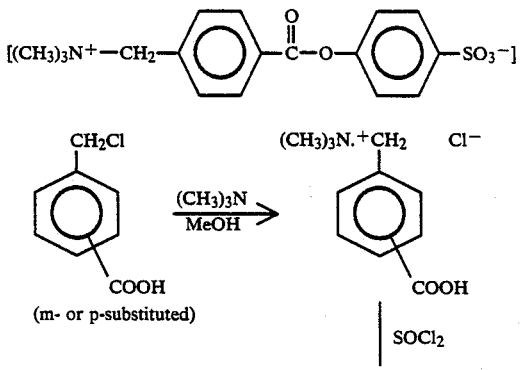

water (500 ml). The product separated out of solution was filtered and washed with water. Total dry yield 73 g (60%). This material was crystallized from water 2:1 isopropanol to give 65 g, which is 'HNMR assayed at 92% purity.

SCHEME 2

Synthesis of:

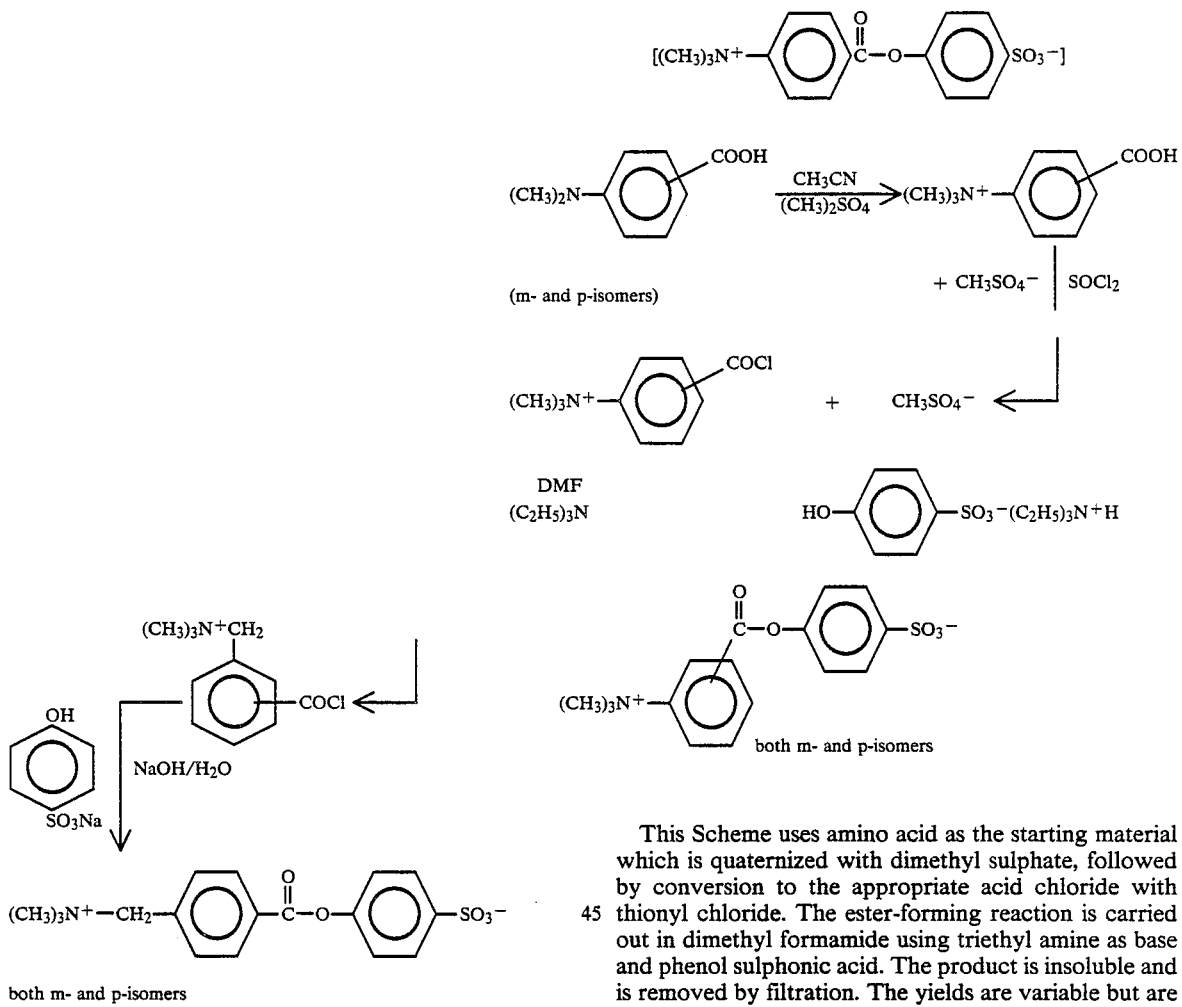

This Scheme is a two-step process starting from the appropriate chloromethyl benzoic acid. The quaternization gives a high yield (90–95%) and the coupling of the acid chloride in water, wherein the product precipitates, also gives good yields of about 85%.

DESCRIPTION OF PROCESS

α-Chloro-p-toluic acid (60 g, 0.35 m) was heated under reflux in methanolic trimethyl amine (35% soln., 200 ml) for a period of 4 hours. The product was concentrated under reduced pressure and acidified with hydrochloric acid 5 m (pH 2), then concentrated to dryness. To this solid, thionyl chloride (100 ml) was added and the mixture heated under reflux for 30 min. The excess of thionyl chloride was removed under reduced pressure yielding the acid chloride. This acid chloride (100 g) was used without further purification in 2×50 g batches with phenol sulphonic acid sodium salt (56 g; excess) with sodium hydroxide (9.2 g; excess) in This Scheme uses amino acid as the starting material which is quaternized with dimethyl sulphate, followed by conversion to the appropriate acid chloride with thionyl chloride. The ester-forming reaction is carried out in dimethyl formamide using triethyl amine as base and phenol sulphonic acid. The product is insoluble and is removed by filtration. The yields are variable but are usually greater than 60%.

DESCRIPTION OF PROCESS

3-N,N-Dimethylamino benzoic acid (16.5 g, 0.1 m) was dissolved in acetonitrile (100 ml) heated under reflux with dimethyl sulphate (12.6 g, 0.1 m) for 6 hours. The quaternary salt crystallized and was separated by filtration (25 g; 86%). This salt (5 g, 0.017 m) was dissolved in thionyl chloride (15 ml) and heated under reflux for 2 hours. The thionyl chloride was removed under reduced pressure and the acid chloride was added to dry DMF containing phenol sulphonic acid triethyl ammonium salt (7.7 g) and triethyl amine (2.5 g). The mixture was stirred and cooled. The product precipitated out of solution was removed by filtration and washed with methanol. The solid (3.3 g, 58%) was dried.

SCHEME 3

Synthesis of:

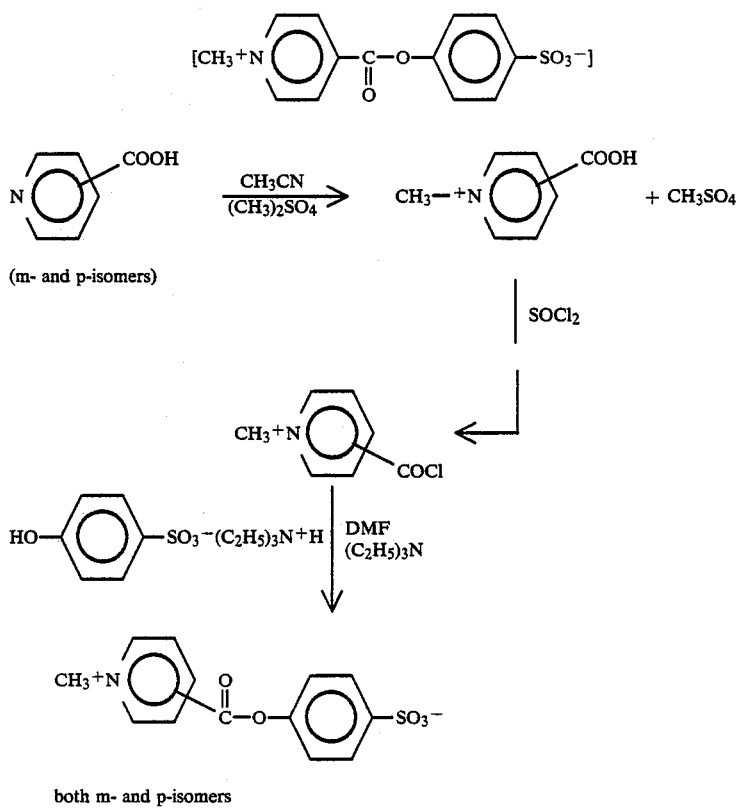

This Scheme is similar to Scheme 2 using the amino acid as starting material with yields that are variable but are usually greater than 60%.

DESCRIPTION OF PROCESS

Nicotinic acid (36.9 g, 0.3 m) was added to 'spectrosil' acetonitrile (200 ml) containing dimethyl sulphate (37.8 g, 0.3 m) and the mixture was heated under reflux for 8 hours. After cooling, the product crystallized out of solution was separated by filtration and washed with acetonitrile. The yield was 56 g, 75%.

The n-methyl nicotinic acid methosulphate (10 g; 0.04 m) was dissolved in thionyl chloride (15 ml) and heated under reflux for 1 hour. The thionyl chloride was removed under reduced pressure. This acid chloride was dissolved in anhydrous DMF (15 ml) containing triethyl amine (10 g) and triethyl ammonium salt of 4-hydroxy benzene sulphonic acid (17 g). The mixture was sonicated and a precipitate formed over 1 hour. This precipitate was separated by filtration and washed with methanol. The solid was dried under vacuo, which is 'HNMR assayed at 94% purity.

SCHEME 4

Alternative synthesis of:

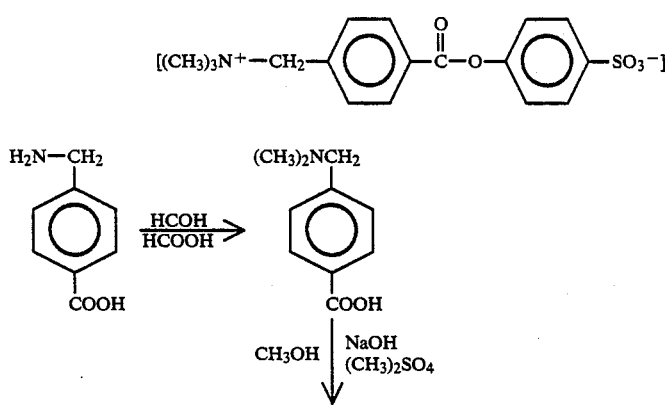

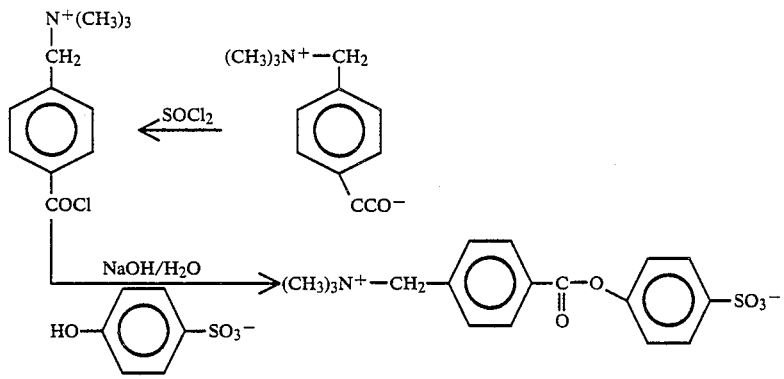

Scheme 1 and Scheme 4 were used for scale-up production quantities of about 2 kg. The overall yields for the scale-up reactions were 86% and 67% for Schemes 1 and 4, respectively. The purity of the materials obtained was high, viz. 97% and 93%, respectively.

EXAMPLES

Two series of bleaching tests were performed on tea-stained cotton test cloths in a Tergotometer under isothermal wash conditions, for 30 minutes, using bleach precursor at a concentration of 1.2 mM and hydrogen peroxide at a concentration of 12 mM, resulting in a peroxide precursor ratio of 10:1.

One series was performed at 40° C. and pH 9.3 and another series at 22° C. and pH 8.

The experiments were performed with five quaternary ammonium peroxy carboxylic acid precursor compounds (ii), (iii), (iv), (v) and (viii) of the invention, which were compared with a quaternary ammonium peroxy carboxylic acid precursor compound (A), N,N,N',N'-tetraacetyl ethylene diamine (TAED) and sodium benzoyloxy benzene sulphonate (SBOBS) of the art.

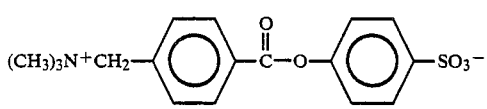
(ii)

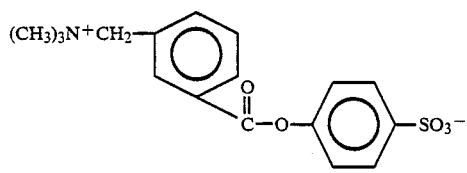
(iii)

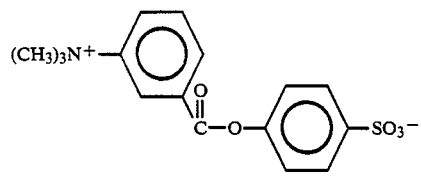
(iv)

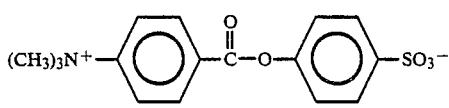
(v)

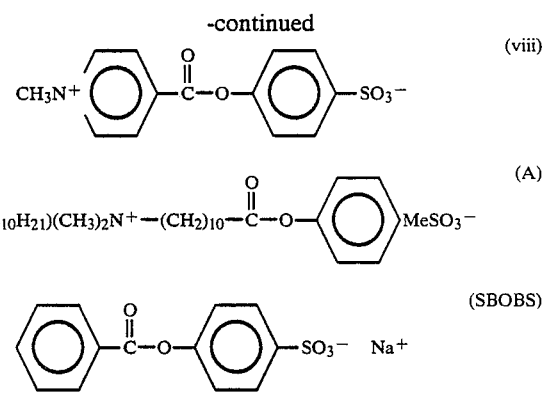

The bleaching efficiencies were determined using an Elrepho reflectometer and the results expressed as $\Delta R$ (460 nm) are shown in the following Table.

TABLE

| Precursor compound | $\Delta R$ (460 nm) | |
| --- | --- | --- |
|  | 40° C./pH 9.3 | 22° C./pH 8 |
| (ii) | 28.1 | 24.1 |
| (iii) | 28.1 | 26.0 |
| (iv) | 27.7 | 24.2 |
| (v) | 23.3 | 13.0 |
| (viii) | 20.3 | 25.3 |
| (A) | 16.9 | 6.8 |
| TAED | 3.5 | 3.0 |
| SBOBS | 9.0 | 11.0 |

From these data the superior performance of the precursor compounds of the invention over compound (A), TAED and SBOBS are clearly seen.

When these experiments were repeated in the presence of a conventional phosphate built detergent base powder, it was found that the same good performances were observed with the precursor compounds (ii), (iii), (iv), (v) and (viii) of the invention, whereas with precursor (A), $\Delta R$ was found to be reduced from 16.9 to 9.0.

This suggests that there is no incompatibility of the precursors (ii), (iii), (iv), (v), (viii) with the components of the detergent base powder. On the other hand, there are evidently antagonists interactions of precursor (A) or its intermediate species with the anionic components of the detergent formulation.

We claim:
1. A bleaching-detergent composition comprising:
   (i) from 2 to 40% by weight of a peroxide bleaching compound capable of yielding hydrogen peroxide in aqueous solution;

(ii) from 0.1 to 20% by weight of a peroxycarboxylic acid precursor having the formula:

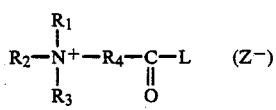

wherein $R_1$, $R_2$ and $R_3$ are each a radical selected from the group consisting of alkyl, alkenyl, hydroxyalkyl and polyoxyalkylene containing from 1 to 18 carbon atoms;

or two or more of $R_1$, $R_2$ and $R_3$ together with the N-atom form an optionally substituted, nitrogen-containing heterocyclic ring system;

$R_4$ is a bridging group selected from

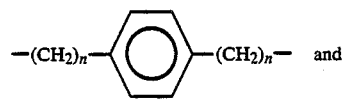

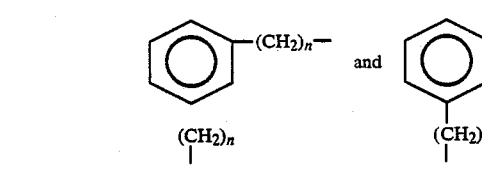

wherein each n can individually be 0, 1 or 2;

L is a leaving group, the conjugate acid of which has a p$K_a$ in the range of from 4 to 13, and $Z^-$ can be a chloride, bromide, hydroxide, nitrate, methosulphate, bisulphate, acetate, sulphate, citrate, borate or phosphate anion;

(iii) from 0 to 50% by weight of a surface-active material selected from the group consisting of anionic, nonionic, amphoteric, zwitterionic and cationic surfactants and mixtures thereof;

(iv) from 0 to 80% by weight of a detergency builder.

2. A bleaching-detergent composition according to claim 1, wherein L has the formula:

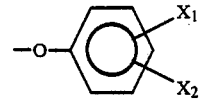

wherein $X_1$ and $X_2$ are each individually H or a substituent selected from $-SO_3^-M^+$; $-COO^-M^+$; $-SO_4^-M^+$; $-(N^+R_1R_2R_3)Z^-$; $-NO_2$; and $C_1$-$C_8$ alkyl groups, wherein $M^+$ is selected from the group consisting of hydrogen, alkali metal, ammonium, or alkyl or hydroxyalkyl-substituted ammonium cation.

3. A bleaching-detergent composition according to claim 2, wherein the precursor is of the formula:

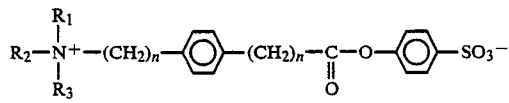

4. A bleaching-detergent composition according to claim 3, wherein $R_1$, $R_2$ and $R_3$ are $C_1$-$C_4$ alkyl groups.

5. A bleaching-detergent composition according to claim 4, wherein $R_1$, $R_2$ and $R_3$ are methyl groups.

6. A bleaching-detergent composition according to claim 1, wherein the p$K_a$ of the conjugate acid of L is in the range from about 8 to 10.

* * * * *